(12) United States Patent
Merz

(10) Patent No.: US 8,597,936 B2
(45) Date of Patent: Dec. 3, 2013

(54) DEVICE AND METHOD FOR THE AUTOMATED AND REPRODUCIBLE PRODUCTION OF CELL OR TISSUE SAMPLES THAT ARE TO BE ANALYZED AND ARE ARRANGED ON OBJECT SUPPORTS

(76) Inventor: Harmut Merz, Groβ Grönau (DE)

( * ) Notice: Subject to any disclaimer, the term of this patent is extended or adjusted under 35 U.S.C. 154(b) by 745 days.

(21) Appl. No.: 12/301,550

(22) PCT Filed: May 18, 2007

(86) PCT No.: PCT/EP2007/004461
§ 371 (c)(1),
(2), (4) Date: Nov. 19, 2008

(87) PCT Pub. No.: WO2007/134814
PCT Pub. Date: Nov. 29, 2007

(65) Prior Publication Data
US 2009/0162862 A1  Jun. 25, 2009

(30) Foreign Application Priority Data

| May 19, 2006 | (DE) | .......................... 10 2006 023 626 |
| Apr. 16, 2007 | (DE) | .......................... 10 2007 017 807 |

(51) Int. Cl.
| *C12M 1/00* | (2006.01) |
| *C12M 1/34* | (2006.01) |
| *C12M 3/00* | (2006.01) |
| *C12Q 1/68* | (2006.01) |
| *B01L 9/00* | (2006.01) |

(52) U.S. Cl.
USPC .................. 435/283.1; 435/287.2; 435/288.7; 422/50; 422/563

(58) Field of Classification Search
USPC ............ 435/283.1, 287.2, 288.7; 422/50, 563
See application file for complete search history.

(56) References Cited

U.S. PATENT DOCUMENTS

| 4,647,543 A | | 3/1987 | Stocker |
| 4,911,915 A | * | 3/1990 | Fredenburgh .............. 435/40.52 |

(Continued)

FOREIGN PATENT DOCUMENTS

| EP | 0117262 | 9/1984 |
| EP | 1370639 | 2/2003 |

(Continued)

OTHER PUBLICATIONS

Lossos et al. "Prediction of Survival in Diffuse Large-B-Cell Lymphoma Based on Expression of Six Genes." New England Journal of Medicine, 2004; 350: 1828-37.

(Continued)

*Primary Examiner* — Robert T. Crow
(74) *Attorney, Agent, or Firm* — Pearne & Gordon LLP

(57) ABSTRACT

An automatically operating apparatus designed as a table-top apparatus for the reproducible production of cell or tissue samples to be examined and arranged on specimen slides comprises, located its center, a rotatably supported, advance device having arranged on its periphery a plurality of modular processing stations at a distance from the advance device. Receiving devices provided in the peripheral region of the advance device are disposed to receive specimen slides on which automatically segmented cell and tissue segments can be positioned in a reproducible and correctly aligned manner. The cell and tissue segments are durably fixed in position on the specimen slides with the use of a curable adhesive, and the specimen slides, after being delivered, are subjected to further treatment processes in a further treatment device.

39 Claims, 14 Drawing Sheets

(56) References Cited

U.S. PATENT DOCUMENTS

| | | | |
|---|---|---|---|
| 5,320,808 A * | 6/1994 | Holen et al. | 422/64 |
| 5,690,892 A * | 11/1997 | Babler et al. | 422/63 |
| 6,093,574 A * | 7/2000 | Druyor-Sanchez et al. | 436/180 |
| 6,251,516 B1 * | 6/2001 | Bonner et al. | 428/346 |
| 2002/0031833 A1 * | 3/2002 | Heyneker et al. | 436/46 |
| 2003/0022271 A1 * | 1/2003 | Voneiff et al. | 435/40.52 |
| 2003/0032191 A1 * | 2/2003 | Hilson et al. | 436/47 |
| 2003/0056729 A1 * | 3/2003 | Correa et al. | 119/6.8 |
| 2004/0026938 A1 | 2/2004 | Junge | |
| 2005/0221271 A1 * | 10/2005 | Murphy et al. | 435/4 |
| 2005/0273131 A1 * | 12/2005 | Shluzas et al. | 606/198 |
| 2006/0046282 A1 * | 3/2006 | Hewitt | 435/40.5 |

FOREIGN PATENT DOCUMENTS

| | | |
|---|---|---|
| WO | WO0122086 | 3/2001 |
| WO | WO01/31317 | 5/2001 |
| WO | WO2004/039938 | 5/2004 |
| WO | WO 2005/073693 | 8/2005 |

OTHER PUBLICATIONS

Kanonen, J. et al. "Tissue Microarrays for High-Throughput Molecular Profiling of Tumor Specimens", Nature Medicine, Nature Publishing Group, New York, NY, US, vol. 4, No. 7, Jul. 1998, pp. 844-897, XP002934472, ISSN: 1078-8956.

\* cited by examiner

DEVICE AND METHOD FOR THE AUTOMATED AND REPRODUCIBLE PRODUCTION OF CELL OR TISSUE SAMPLES THAT ARE TO BE ANALYZED AND ARE ARRANGED ON OBJECT SUPPORTS

CROSS-REFERENCE TO RELATED APPLICATIONS

The present Application is based on International Application No. PCT/EP2007/004461, filed on May 18, 2007, which in turn corresponds to German Application No. 102007017807.9, filed on Apr. 16, 2007 and German Application No. 102006023626.2, filed on May 19, 2006, and priority is hereby claimed under 35 USC §119 based on these applications. Each of these applications are hereby incorporated by reference in their entirety into the present application.

FIELD OF THE INVENTION

The invention relates to an apparatus for the automated, reproducible production of cell or tissue samples to be examined and arranged on specimen slides, in particular of patient material, whereby the apparatus comprises a plurality of modular stations, each performing a process step as part of a total sequence of process steps and to a suitable specimen slide for use in the inventive apparatus. In addition, the invention relates to a method for the production of such samples.

BRIEF DESCRIPTION OF THE RELATED ART

In the recent past, the improvement of analytical genetic engineering methods resulted in an increased need of tissue examinations. In particular, in the field of oncology in the treatment and diagnosis of cancer, gene expression analysis there is an increasing reliance on gene expression analysis. By using such an analysis, use is made of the fact that of the 25,000 existing genes of the human genome, there are frequently only 200 to 300 that are determinants for the function of a tumor. In turn, frequently 20 to 30 genes can be extracted from these characteristic genes which, without significant deterioration of the statistical evidence, are able to provide reliable information regarding the status of the tumor, the effect of a treatment and the course of the disease. Gene expression analysis is used to examine tumors to determine whether special genes are switched on/off or what genes are present. This is accomplished with cell or tissue samples that are assayed by means of special antibodies, said antibodies— by using staining techniques—subsequently providing specific evidence of the genes in the tissue.

Arrangements and methods that have been known until now such as are disclosed, for example, in patent documents EP 1370639 and WO 01/22086, use tissue fields that consist of field arrays of different tissue samples and, at the same time, are exposed to an agent with which a specific antibody can be applied to the different tissue samples. Upon subsequent staining, all of the different tissue samples on the specimen slide may be examined under the microscope.

In the preparation of tissue samples, tissue blocks are first punched out of the tissue to be examined and then placed in a paraffin block. In so doing, the size of the tissue blocks depends on the intended punch diameter. The paraffin blocks are then used to produce so-called array paraffin blocks in that thin sample tubes are used to remove a punched cylinder of the tissue sample located in the paraffin block and to set said punched cylinder—as in a field—into another paraffin block, so that, for example, up to 240 different tissue samples of different origin can be accommodated in such a block. For the subsequent examination, a partial section transverse to the cylindrical axis is performed and thus a thin layer of different tissue samples is obtained, i.e., virtually in the manner of an array embedded in paraffin, whereby said thin layer can be placed on a slide and examined.

Such arrangements and the subsequent assay techniques have the particular disadvantage that they do not allow any individualized, i.e., patient-specific, examinations because the entire sample field, once combined in one wax cylinder, is or must be examined over and over again. Furthermore, another disadvantage of this method consists in that a large number of samples can be examined with only one testing reagent.

However, as mentioned above, there is a great need to perform a plurality of tests on tissue samples of one and the same tissue per patient, whereby these are to be tested with the most varied agents, i.e., with antibodies or probes, for specific genes, for example, in view of the type of cancer.

A serological method testing for antibodies in the blood of a patient has been known from U.S. Pat. No. 4,647,543. This technique is mainly being to diagnose autoimmune diseases in the test persons. In this method, by staining the tissue, antibodies present in the blood are caused to react with indicator tissue that has been specifically treated for this purpose in order to indicate the presence of an antibody-specific type in the blood. In so doing, neither a structural examination of the tissue is performed, nor is it possible with the use of the staining technique used there, to provide a good morphological resolution for the visualization of specific structures of the tissue.

SUMMARY OF THE INVENTION

Embodiments of the invention are directed to an apparatus and a method for the processing of tissue to be examined, as well as a specimen slide for the tissue to be examined, that permit the combined and synchronous processing of several samples of a single tissue in a technically simple manner. In particular, this processing is to permit the simultaneous use of different process techniques. At the same time, the apparatus is to be designed in a simple and robust manner and to ensure continuous operation.

The apparatus in accordance with the invention comprises at least one device for the correct positional arrangement of the samples on the specimen slide and a device for advancing the loaded specimen slide to the individual processing stations, in which case the advance device is advantageously located in the center of the apparatus and has stations for further processing distributed along its periphery.

In so doing, the advance device may be a rotatably supported round table which is cyclically moved at equal time intervals, for example, if several specimen slides are to be advanced at the same time by the advance device, or is continuously moved by program control if the advance device supplies, successively, only one specimen to the individual processing stations. Whereas, when several specimen slides are processed at the same time on different work stations, the clockwise advance must be adjusted in view of the longest dwell time on a work station, the work cycles on the individual work stations may vary when only one specimen slide is put through.

In accordance with another advantageous feature of the invention, the advance device is supported by a pedestal-like housing which accommodates the drive and/or the control for the advance device. Also, in this case, it is possible to connect pneumatic and hydraulic pressure lines that are disposed to supply pressure media to the operating parts of the work station.

Advantageously, the modular processing stations are arranged distributed in an array at constant angles relative to each other along the periphery of the advance device, so that they can be cyclically supplied with specimen slides by means of the advance device. In another advantageous embodiment of the subject matter of the invention, the periphery of the advance device comprises receiving devices in which the specimen slides may be inserted in order to secure them in position during advance. In this case, array devices that have been know per se may be used, these devices permitting a temporary fixation and release of the specimen slides.

The processing stations are arranged on the upper side of the pedestal-like housing, whereby the specimen slides are fed to the device via an input station. Advantageously, this input station is allocated a slide tray from which the specimen slides can be successively supplied. In so doing, it is possible to use trays that are exchangeable and have a storage capacity of at least 150 specimen slides.

Furthermore, the apparatus advantageously comprises a station for fixing the samples in place on a specimen slide, whereby this station comprises a dispenser for an adhesive for the application of discretely positioned metered amounts of adhesive having a defined size onto the specimen slide. By means of known pipetting techniques, the adhesive may be applied in a prespecified grid to the surface of the specimen support, the adhesive preferably being a type of UV adhesive such as, for example, Loctite 3491 (a single component, medium viscosity, fast curing UV adhesive produced by Loctite Corporation USA).

The apparatus advantageously comprises, as the next station, a device for supplying a sample film provided with cell or tissue sections, said film consisting of a first transparent substrate, to a specimen slide, and comprises a punch for segmenting the samples, and a device for separating the samples. The supply device, the punch and the separating device are combined in one work station.

Advantageously, the separating device comprises a plate cam by means of which a plurality of picking devices can be moved over curved paths out of an essentially central position into a defined position at a distance relative to each other. In so doing the picking devices consist of cylinders with pneumatically actuated suction cups. The separating device is supported so as to be movable between the punch and the specimen slide.

After the sample film consisting of the first transparent substrate provided with the cell or tissue sections has been moved automatically from the outside into the feeding device, the punch stamps the samples out of the sample film, whereby said punch moves from the underside toward the picking devices that are pressed against the film above said film, and that act as abutments. While the segmented punched-out film pieces are held by the suction cups that are subjected to a vacuum, the separating device is moved away toward the grid-like specimen slide, whereby the cylinders move at the same time as the pneumatically actuated suction cups over the curved paths toward the outside and thus correctly position the segmented samples in the grid of the specimen slide.

After the samples have been set on the specimen slide by means of the picking devices and are prevented from being displaced by the drop-shaped UV adhesive, the specimen slide is transferred to another processing station where the adhesive is cured by the effect of irradiation with UV light. After the adhesive has fully cured, the specimen slide is transferred to an inscribing and/or labeling station, in which the specimen slide is inscribed with a barcode or labeled. Finally, it is also advantageously possible to provide a camera station for the visual detection of the individual samples and for the selection of suitable samples, as well as for the separation of unsuitable sample material.

When the specimen slide with the segmented and correctly positioned and aligned samples is completed, it is transferred to a delivery station, in which the finished specimen slides are delivered to a subsequent device, in which the samples on the specimen slide are heated or stained, for example.

Furthermore, the apparatus may advantageously comprise a control panel that can be used to adjust controls for the adjustment of the process modes on the procession stations. The housing of the apparatus comprises a frame of aluminum profiles, said frame being provided with a removable cover required to prevent operator intervention. This setup permits high flexibility and saves weight, because the apparatus is designed as a table-top apparatus to ensure easy transport.

It is particularly advantageous when the specimen slide in accordance with the invention is an array-like specimen slide that has several equally dimensioned reaction zones, whereby individual tissue/substrate units are accommodated in reaction zones, whereby the substrate is flexible and transparent, and whereby the respective reaction zones are provided with hydrophobic borders.

In this way, a standardized test carrier medium is provided that can be used for the application of different processing fluids with pipettes when special gene expression analyses are performed on tissue material.

In another particularly advantageous manner, a development of the specimen slide in accordance with the invention provides that a cover can be applied over the reaction zones of the specimen slide in order to preserve the specimen slide or the tissue/substrate units in the reaction zones for later observation.

In a further particularly advantageous manner, a development of the specimen slide in accordance with the invention provides that the overall thickness of the slide does not exceed the distance between a specimen slide of a light-optical microscope and its ocular lens tube.

Furthermore, in yet another advantageous manner, a development of the specimen slide in accordance with the invention provides that the height of the border of a reaction zone and the thickness of the substrate, as well as any tissue located thereon, be adjusted relative to each other in such a manner that any desired processing with the reaction fluid may still occur, but that the amount of fluid applied is as exact as possible to be sufficient for a reaction for processing, so that none of the more expensive fluids need to be wasted and/or that a commercially available standardized fluid volume can be used for processing more samples than has been possible until now.

Considering a particularly advantageous development, the specimen slide is configured in such a manner that the distance of the reaction zones corresponds to the distance of standardized pipette carriers, because, in this manner, several reaction fluids can be simultaneously dispensed into the different reaction zones in order to subject the specimen slides provided with the samples—after they have been completed—to a subsequent stain treatment by introducing reaction fluids.

In accordance with an advantageous development of the specimen slide, said slide has a text field in which an identification code, in particular in the form of a barcode, can be applied. The identification code can be used to later allocate the specimen slides containing the cell or tissue sections to be assayed to the individual patient.

Advantageously, the reaction zones of the specimen slides are formed by coating the slide with a sprayed-on frame or with a film of a different hydrophobic material in which the reaction zones are recessed.

In a particularly advantageous manner, the inventive apparatus and the inventive specimen slide are used for gene expression assays of human cell tissue.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein.

DETAILED DESCRIPTION OF THE PREFERRED EMBODIMENTS

Figure 1:
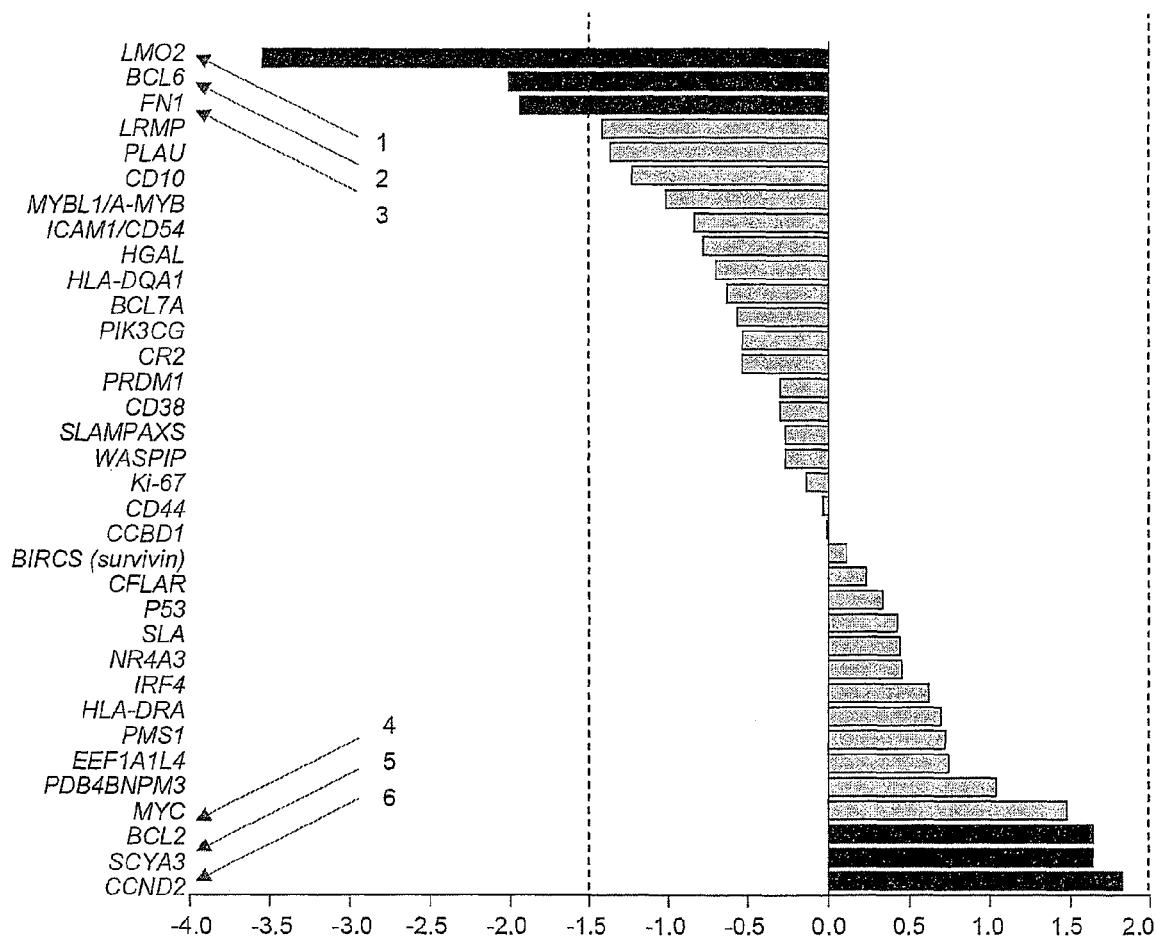
FIG. 1 an example of a quantity of genes to be assayed.

With reference to an example, FIG. 1 shows the variety of genes to be examined in a specific type of cancer. Details of the illustration have been taken from the article by Lossos et al., "Prediction of Survival in Diffuse Large-B-Cell Lymphoma Based on the Expression of Six Genes," New England Journal of Medicine, 2004; 350: 1828-37.

The terms "process" and "processing" that are frequently used in the course of this description of the invention are also intended to mean a step-by-step preparation of test tissue for the individual assay stations.

Furthermore, it is particularly obvious from FIG. 1 that the genes A, B and C or D, E and F are statistically particularly significant, so that they may be considered as being representative of the total amount shown here, i.e., to the extent that the validity with respect to the diagnosis of the tissue is concerned.

Here, it is particularly obvious that the genes A, B and C are specifically characteristic in view of the statistically longer survival of a patient, whereas the genes D, E and F are specifically characteristic in view of the statistically shorter survival of a patient.

Referring to the illustration in FIG. 1, it is readily obvious that there is a great need for processing specific tissue, in view of the use of specific antibodies for several genes, for assaying.

In particular, there is also a need to be able to perform this in a technically effective and rapid manner and with the best-possible utilization of existing assay fluids.

Figure 2:
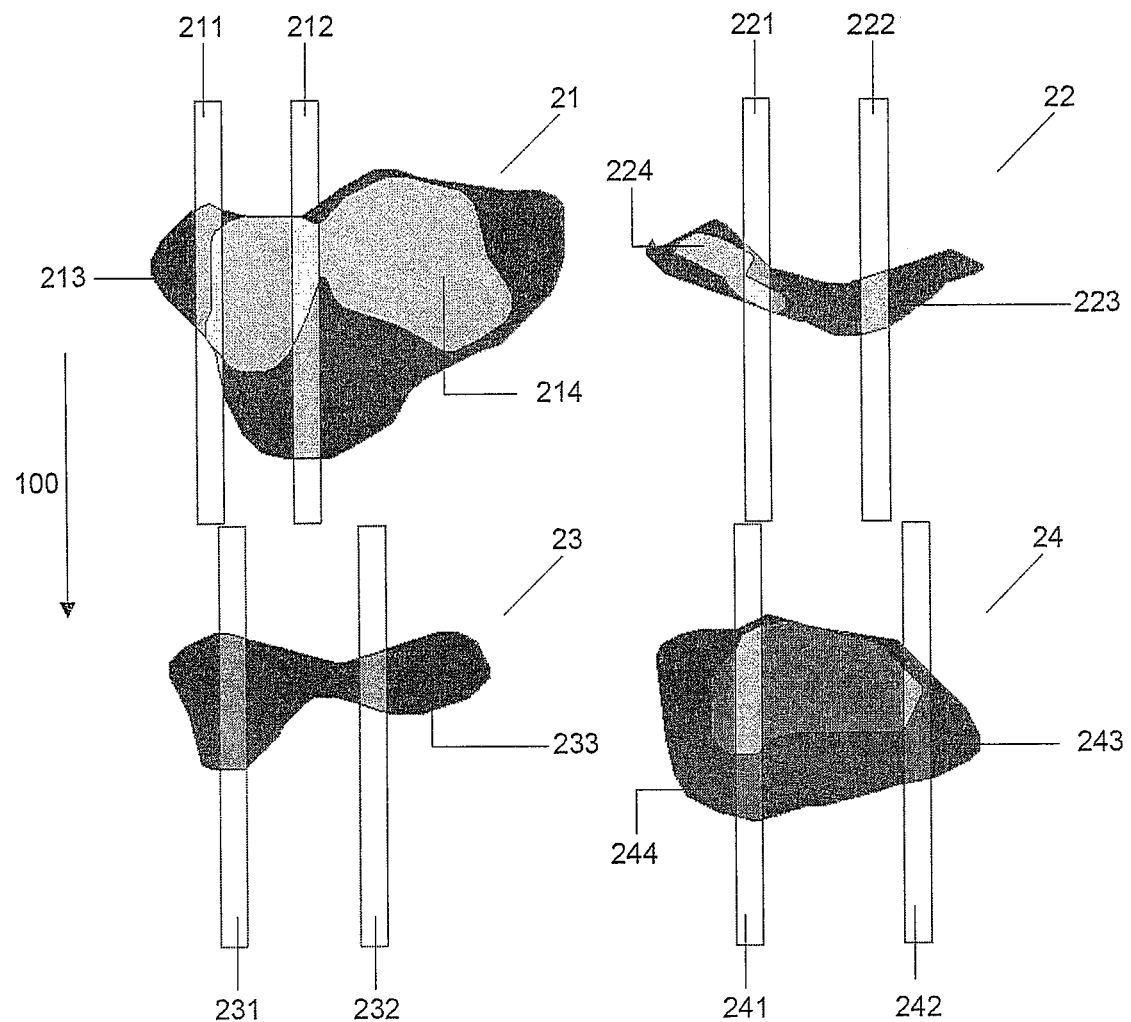
FIG. 2 an example of the removed cylindrical sample of tissue samples embedded in wax cubes.

Referring to an example of different tissue samples, FIG. 2 shows the sample removal in the form of punched cylinders. Such a method has been disclosed, for example, by EP 1370639 A1. As is obvious from FIG. 2, there the individual tissue samples are arranged in paraffin cubes 21, 22, 23 and 24. Here, the paraffin cubes are shown in sections. The cube 21 contains tissue particles 213 and 214; tissue cylinders 211 and 212 being punched out of these. In this instance, punching takes place in a direction 100. The paraffin cube 22 contains tissue components 223 and 224, from which cylindrical samples 221 and 222 are removed.

The paraffin cube 23 contains tissue 233; tissue cylinders 231 and 232 being punched out of it. The paraffin cube 24 contains tissue 244 and 243; tissue cylinders 241 and 242 being punched out of it.

It can already be clearly seen that the tissue is inhomogeneous considering its tissue composition, for example, at 213 and at 214, and also displays a varying depth extension, so that, in part, more or less tissue comes to be located in the individual punched cylinders during the punching operation. Referring to the punched cylinders 212 and 241, particularly much tissue is removed, whereas in the case of the punched cylinders 221 and 222, less tissue is removed. It is also clearly obvious that, considering the depth extension of the cylinders, for example in the region of the cylinder 212, different tissue layers come to be superimposed in the direction 100 of the depth range.

Figure 3:
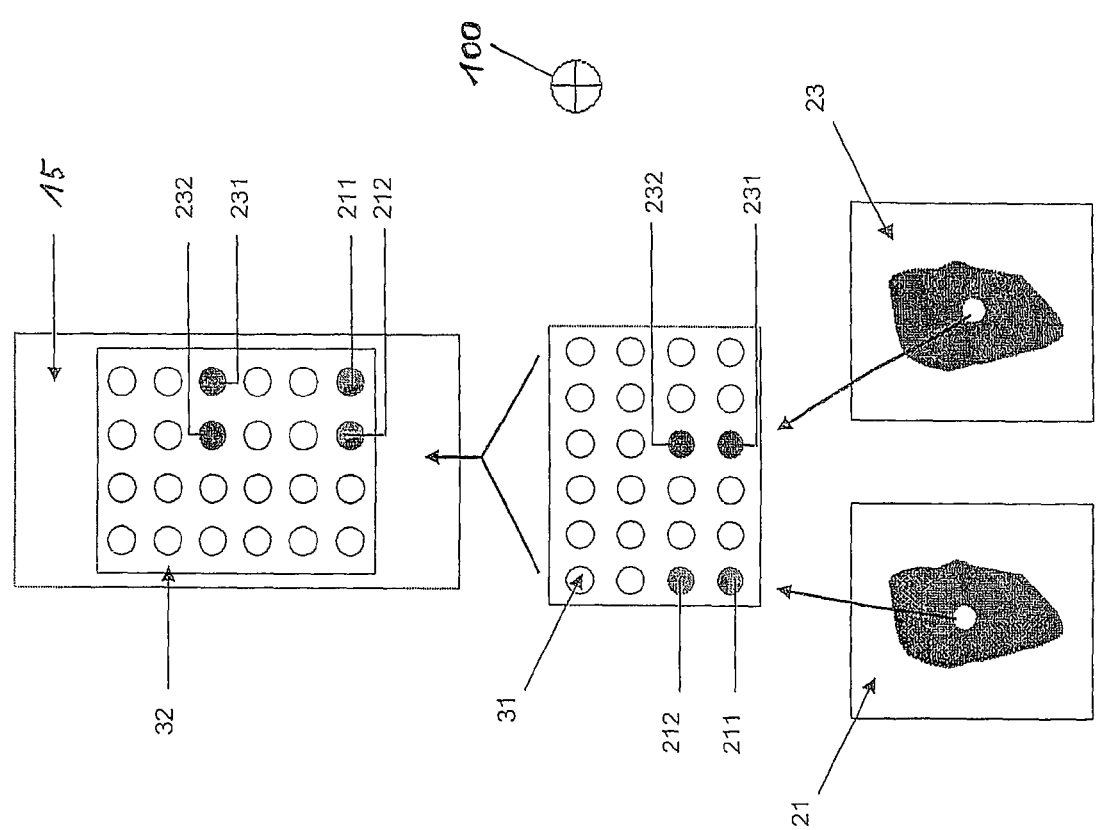
FIG. 3 processing of tissue sample arrays and the application of the tissue sample field on a slide.

FIG. 3 is another view to illustrate how removed cylindrically punched samples embedded in paraffin cubes become sample arrays that can be applied to a specimen slide.

Analogously to FIG. 2, again paraffin cubes 21 and 23 are shown, from which sample cylinders 211 and 212, respectively, and 231 and 232, respectively, are removed. Here, the direction 100 represents the plane of projection. As is further obvious, the cylinders removed from the paraffin cubes 21 and 23 are arranged—as in a field, at regular distances—in another paraffin cylinder 31, so that a sample block is produced, said block containing punched cylinders of the most diverse tissues. By making perpendicular cuts in the direction 100, a thin layer of tissue material can be separated from this sample block and placed on a specimen slide 15. This thin layer 32 is shown on the right in FIG. 3. Such a processing method has been disclosed by the state of the art as represented by WO 01/22086. It is particularly obvious from FIG. 3 that, considering this conventional processing technology, always a plurality of samples of different tissues are arranged on one specimen slide. Furthermore, this processing method has the disadvantage that all the tissue samples that are present together on the specimen slide 15 must be subjected together to a reaction because no measures are taken to separately examine the samples. Apart from this, the state of the art currently includes no method for staining the tissue samples in a different and separate manner. Rather, current apparatus only intend that such specimen slides be subjected in large quantities, step-by-step, to a single treatment.

The disadvantages of these methods are that they are time-consuming, that they consume large quantities of fluid, and that they do not permit any individual assays.

Figure 4:
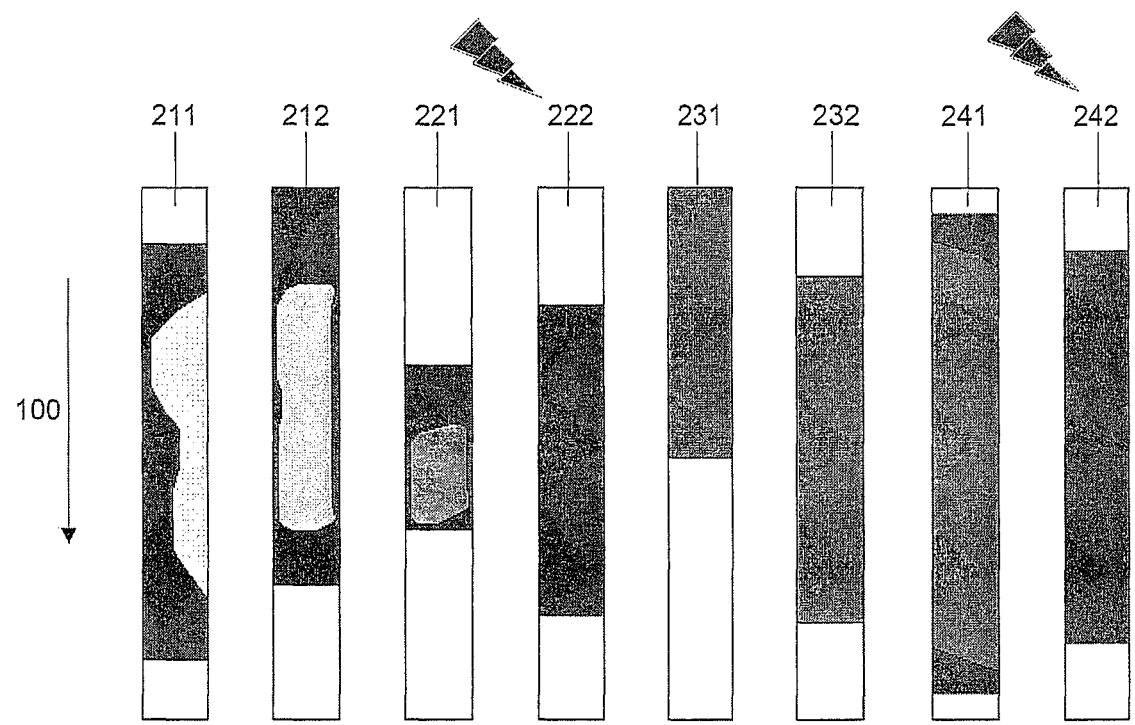
FIG. 4 an illustration of the problems during the examination of punched cylindrical samples that are combined in one tissue array.

Referring to the depth extension in a direction 100 of the different punched cylinders 211, 212, 221, 222, 231, 232, 241 and 242, FIG. 4 illustrates another problem in processing tissue samples in the manner of tissue fields as described in FIG. 3. In this case, the punched cylinders have reference signs analogous to FIG. 2. Looking at the depth extension of the individual cylinders in the direction 100, it is obvious that, for example, considering a section located close to the top in the direction where the reference signs are applied, no tissue can be obtained but only paraffin, for example, in the case of the cylinders 221 and 222. As a result of this, considering an applicable assay, indeed a layer with tissue of a sample cylinder 212 and 231, respectively, can be examined, but the other tissue samples are lost. In the case of paraffin, this loss is not critical because it is possible to visualize that no tissue is present at this location.

However, another problem consists in that the tissue, which has been removed from the tissue to be examined, for example having the form of a 2.0×2.0 mm×0.2-0.3 mm punched cylinder, is inhomogeneous as to depth as well as to area. This means that cancerous tissue is partially incorporated in healthy tissue and that, depending on the arrangement of the section, different tissue layers can be detected in the horizontal direction as well as in the vertical direction through the punched cylinder.

Referring to the illustration in FIG. 4, healthy tissue is shown dark, and diseased tissue is shown light. This means that, for example, the cylinders 222 and 242 do not contain diseased tissue, whereas—depending on the representation at different cutting depths—the other cylinders randomly contain diseased tissue, i.e., cancer cell tissue, and healthy tissue. Therefore, it is conceivable that—in accordance with the method of processing tissue fields as shown, for example, in FIG. 3—a complete tissue region is obtained on the specimen slide which, even upon optical inspection, does not disclose any paraffin regions, but which will still have individual tissue spots that do not contain any cancer cell tissue. This is particularly disadvantageous because sample examinations are to ensure that a negative result is not based on the examination of the wrong tissue.

Figure 5:
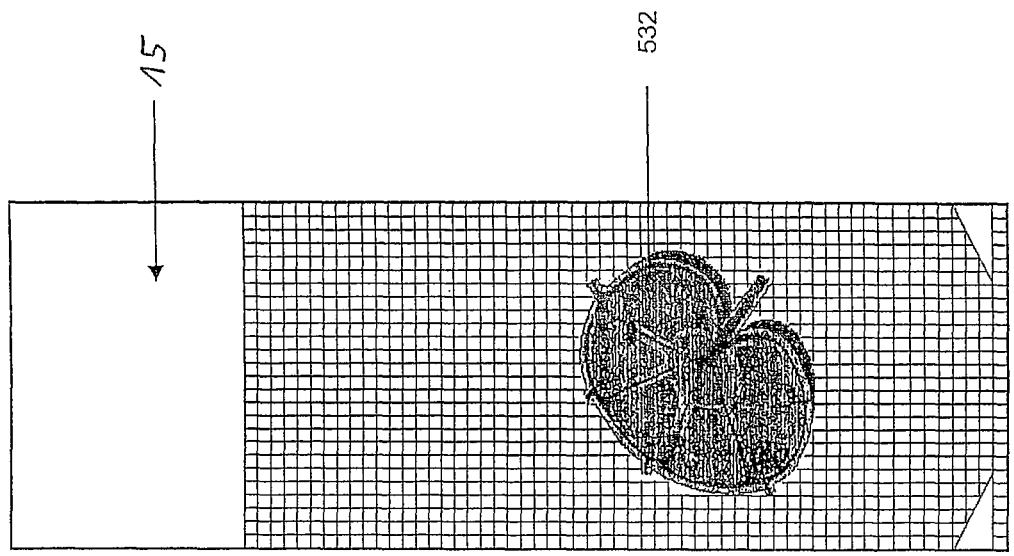
FIG. 5 a tissue sample for staining on a slide.

FIG. 5 shows a specimen slide 15 to which a tissue sample has been applied. The specimen slide 15 carries a planar, cut sample 532, that needs to be stained, for example, by means of a staining technique in order to make specific cell areas visible.

Figure 6:
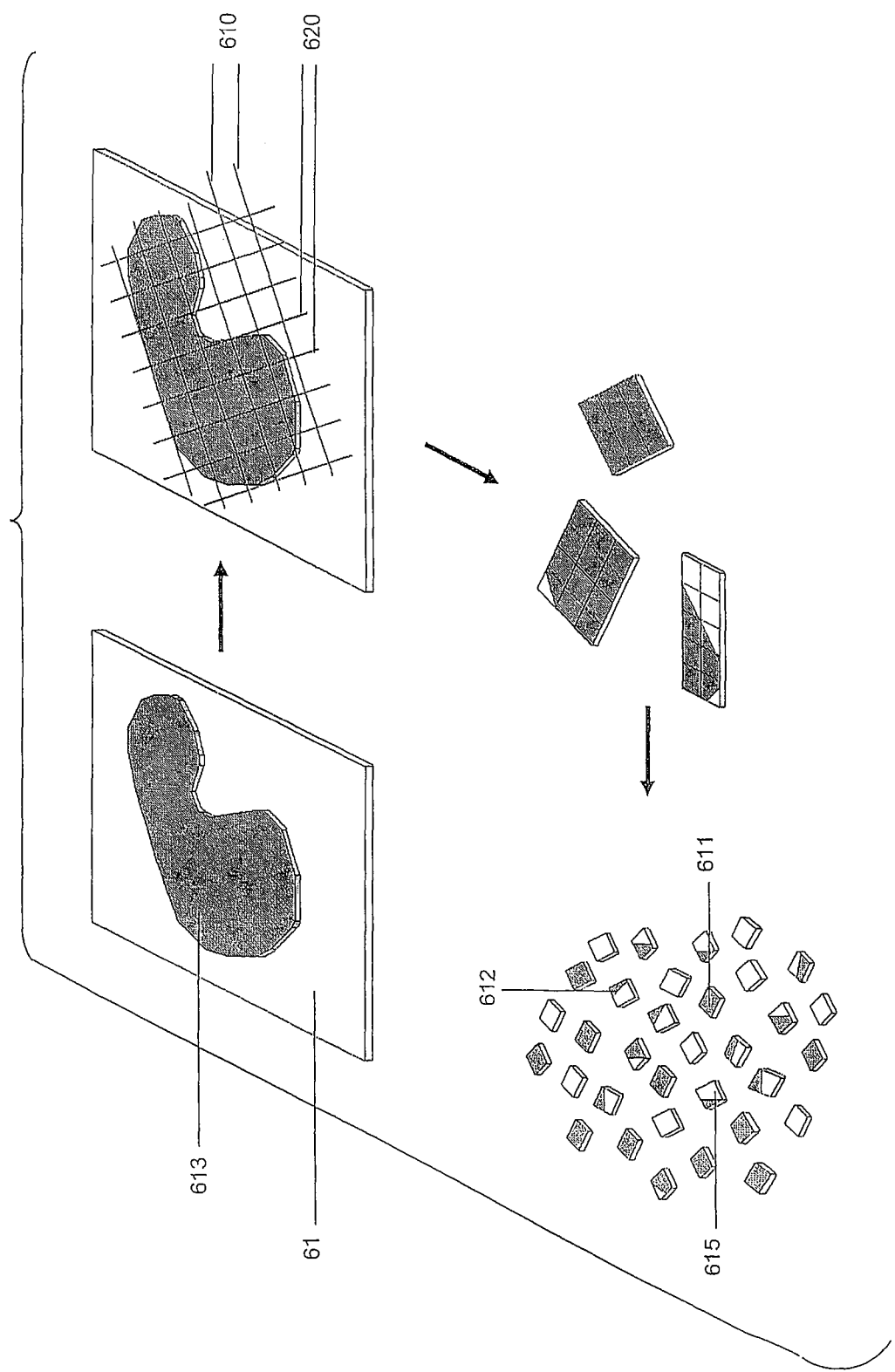
FIG. 6 the division of a planar tissue section mounted to a substrate into individual tissue/substrate units for further processing.

Referring to an example, FIG. 6 shows how a planar tissue section is divided into tissue/substrate units.

FIG. 6 shows a substrate material 61 of the transparent type to which a planar tissue section 613 has been applied. This tissue section 613, for example, has a thickness of 1 to 5 μm and a size of 1×1 cm. Before applying the tissue section to the substrate material that is elastic, for example, and may consist of a polycarbonate film acting as the carrier film, it may be ensured that the tissue is homogeneous, and it may further be ensured by optical inspection that only tissue material relevant to the examination is contained in this tissue section, whereby the disadvantages of prior art previously described with respect to regions in tissue fields can be largely excluded.

As is further shown by FIG. 6, the tissue section 613 is pieced together in the directions 610 and 620, so that subsequently tissue/substrate units 611, 612 and 615 are obtained, only a few of them being shown for visualization. These tissue/substrate units can then be placed in the reaction zones or reaction fields of the specimen slide 15 in order to be able to provide proof of different antigens with the use of various processing reagents.

Figure 7:
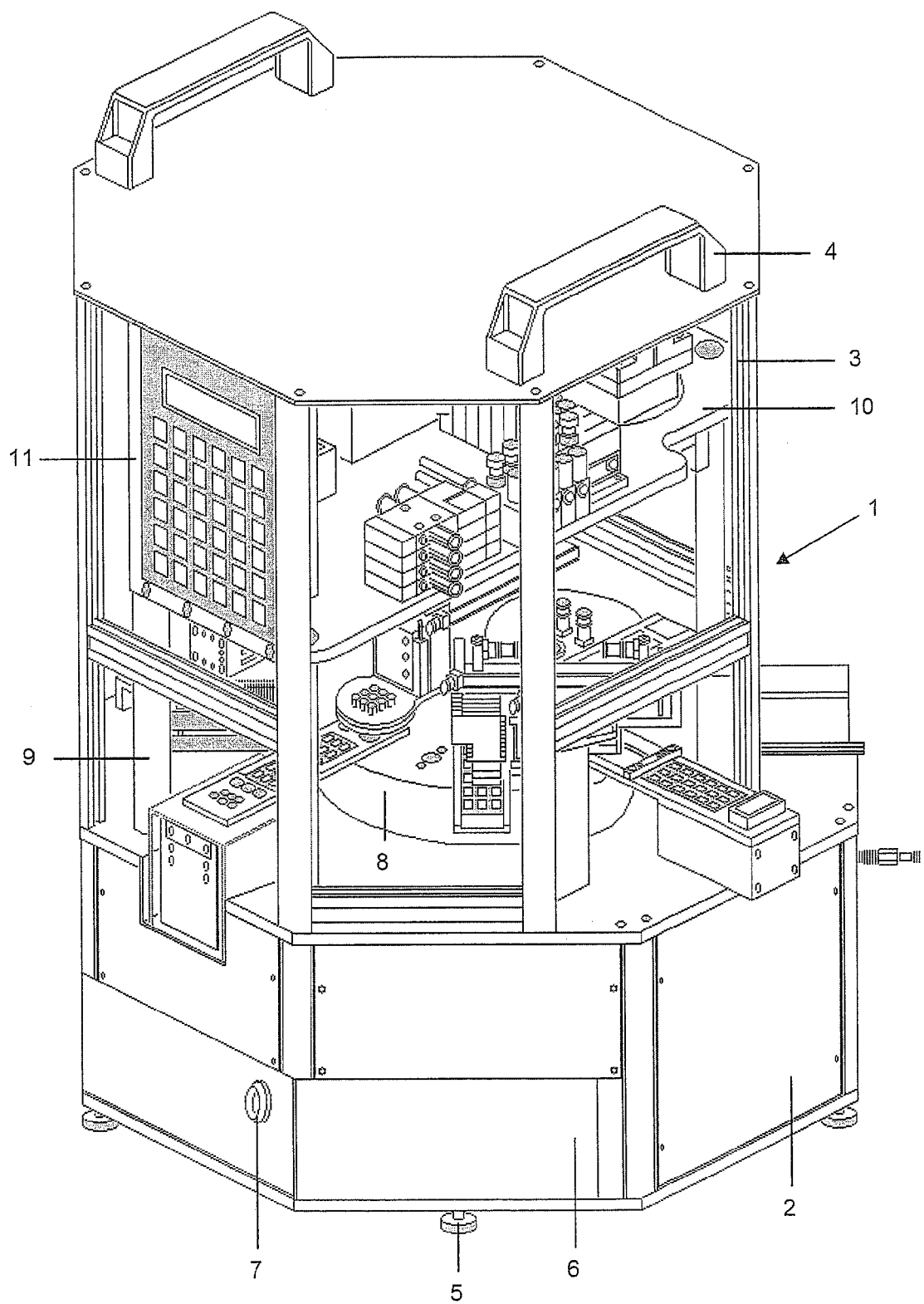
FIG. 7 a perspective general view of the apparatus in accordance with the invention, with the housing cover.

FIG. 7 shows an apparatus in accordance with the invention for the automated, reproducible production of cell and tissue samples that are to be examined and arranged on specimen slides. The apparatus 1 is constructed as a table-top apparatus and essentially consists of a pedestal-like housing 2 on which a removable cover 3 is placed, said cover being interlocked with the pedestal-like housing 2. On its upper side, the cover has two handle units 4, so that the apparatus 1 that is constructed as a table-top apparatus can be transported.

The underside of the pedestal-like housing 2 has adjustable feet 5 that permit the horizontal position adjustment of the table-top apparatus. Advantageously, water levels or similar leveling elements may be provided for exact adjustment, however, these are not shown in the drawing.

Figure 8:
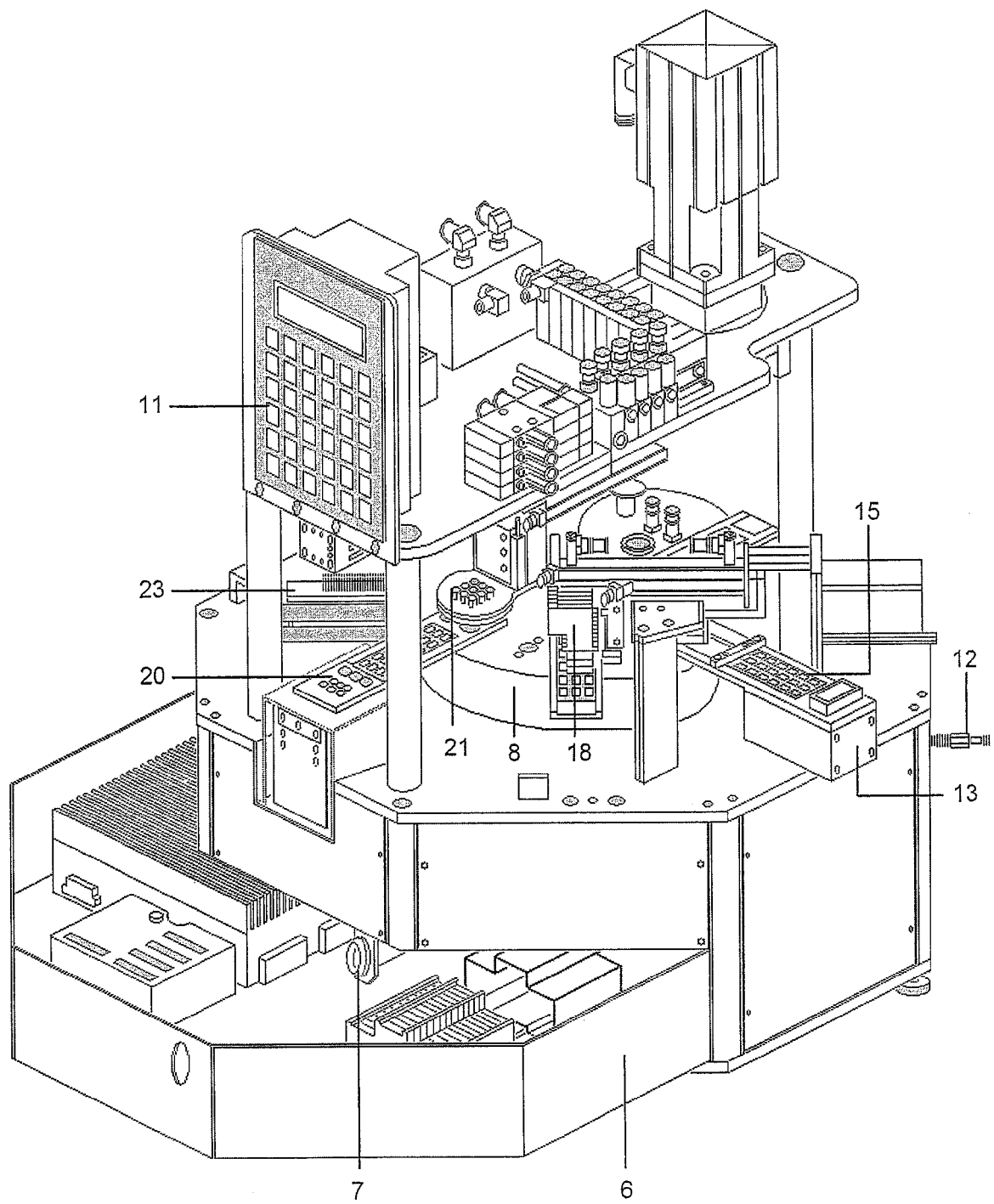
FIG. 8 a perspective general view of the apparatus in accordance with the invention, without the housing cover and opened pedestal.
Figure 9:
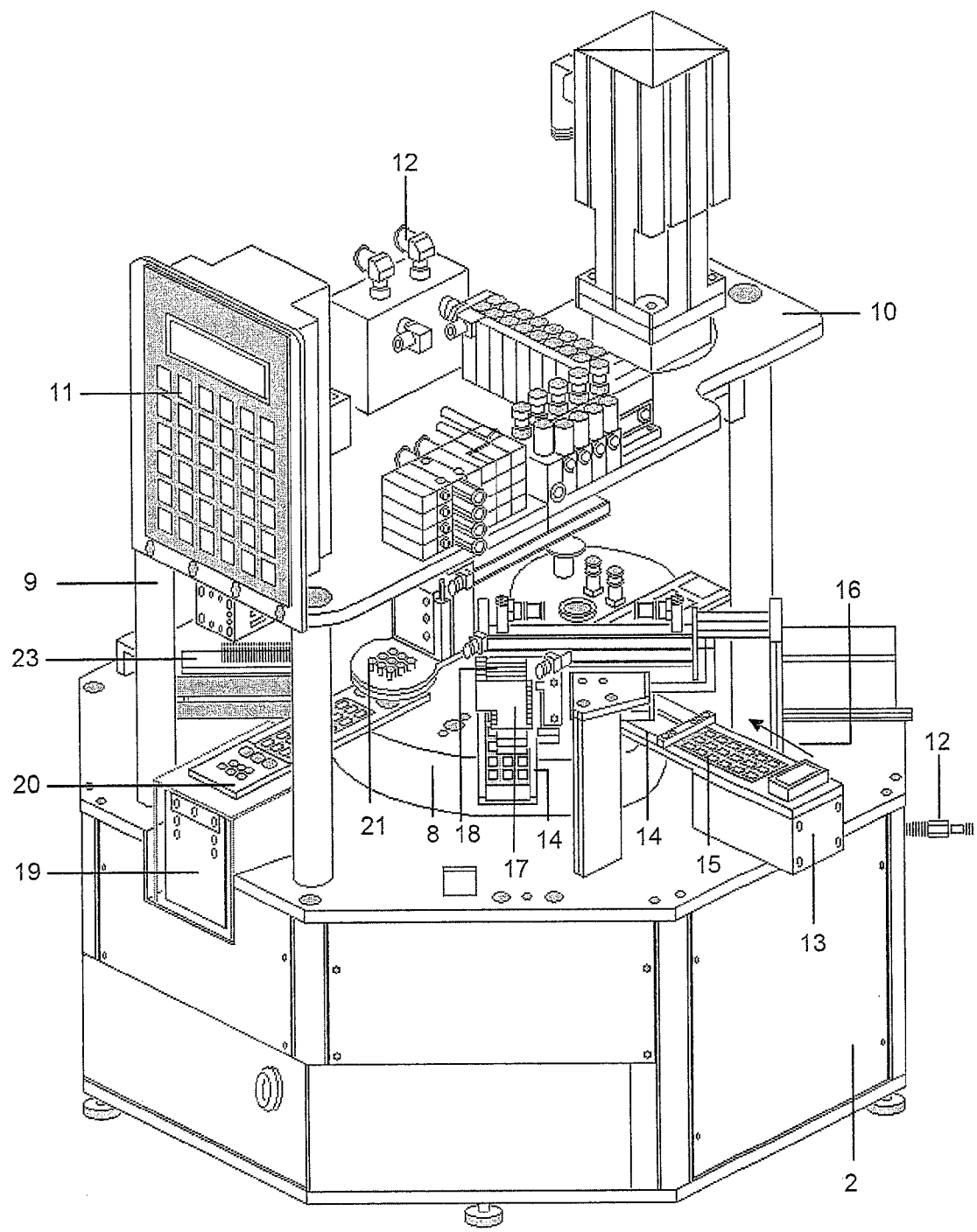
FIG. 9 a perspective general view of the apparatus in accordance with the invention, without the housing cover, slightly rotated in clockwise direction.

Furthermore, a drawer 6 that can be locked with a lock 7 can be seen at the lower side. FIG. 8 shows the drawer 6 in open state, and it can be seen that the control device and part of the driving device for the advance device 8 are arranged in the drawer. The driving device essentially consists of known elements and will not be described in particular here.

On the upper side of the pedestal-like housing 2, a frame 9 of aluminum profiles is provided, whereby, on the upper side of said frame, a plate-like component 10 is supported for the accommodation of additional control components which will not be described in particular and are disposed to control the apparatus components described hereinafter. Operation occurs via a panel 11 on the front side of the inventive apparatus 1, whereby said panel can be used to adjust the operating modes of the processing stations described hereinafter.

Furthermore, the apparatus 1 comprises pneumatic and/or hydraulic pressure connections 12 that are connected to appropriate pressure lines in order to supply the driving components of the processing stations with pressure energy, said components being partially actuated pneumatically/hydraulically.

In the center of the apparatus 1, on the pedestal-like housing 2, the advance device 8 configured as a round table is supported and can be cyclically or continuously rotated by program control. The upper side of the pedestal-like housing 2 has, on the periphery of this advance device, a grid of processing stations arranged at a distance from each other. The loading station 13 feeds the specimen slide 15 in the direction of the arrow 16 to the advance device 8. In so doing, the specimen slide 15 is inserted into one of the receiving devices 14 and fixed in place therein, said receiving devices being provided in the upper edge area in a manner so as to be distributed uniformly at distances on the advance device 8.

As soon as the specimen slide 15 comes into engagement with the receiving device 14 of the advance device 8, the advance device is cyclically moved in clockwise direction until the specimen slide 15 is in registration with the next processing station 17. This is a station for fixing the samples to the specimen slide, in this case a station that is equipped with a dispenser 18 for an adhesive for the application of separately positioned adhesive metered amounts having a defined size onto the specimen slide. Consistent with the prespecified grid of the specimen slide 15, the dispenser 18 places adhesive dots in the individual reaction fields of the grid.

Subsequently, the specimen slide 15 is transferred to the processing station 19 that comprises a punch 20 and a separating device 21. With the use of the punch 20, cell and tissue segments 22 in the form of tissue/substrate units 611, 612 and 615 are punched out of the not illustrated carrier film loaded with cell and tissue sections having a thickness of approximately 1.5 μm, said carrier film being automatically fed from the outside to the apparatus and said substrate units being brought to a distance by means of the separating device and being deposited, by said device, on the specimen slide in the array fields on the adhesive dots in the array fields representing the reaction fields.

As soon as the cell and tissue segments 22 have been deposited on the specimen slide 15, the advance devices 8 is cyclically advanced in clockwise direction and transports the specimen slide 15 to the processing station 23, said station being a curing station for the adhesive. In this station, the specimen slide 15 is irradiated with a UV light source and the adhesive is cured.

The processing station 23 is also followed by an inscribing and/or labeling station that is not shown in the drawing, in which station the specimen slide is provided with a barcode or a label. In addition, there may also be a camera station for the visual detection of the individual samples and for the selection of suitable samples, as well as for the separation of unsuitable material. Finally, the Apparatus comprises, on its rear side, a delivery station that is hidden in the drawing, in which delivery station the finished specimen slides are delivered to a subsequent device for continued processing, where they are subjected to a heat treatment and staining with the use of processing reagents.

Figure 10:
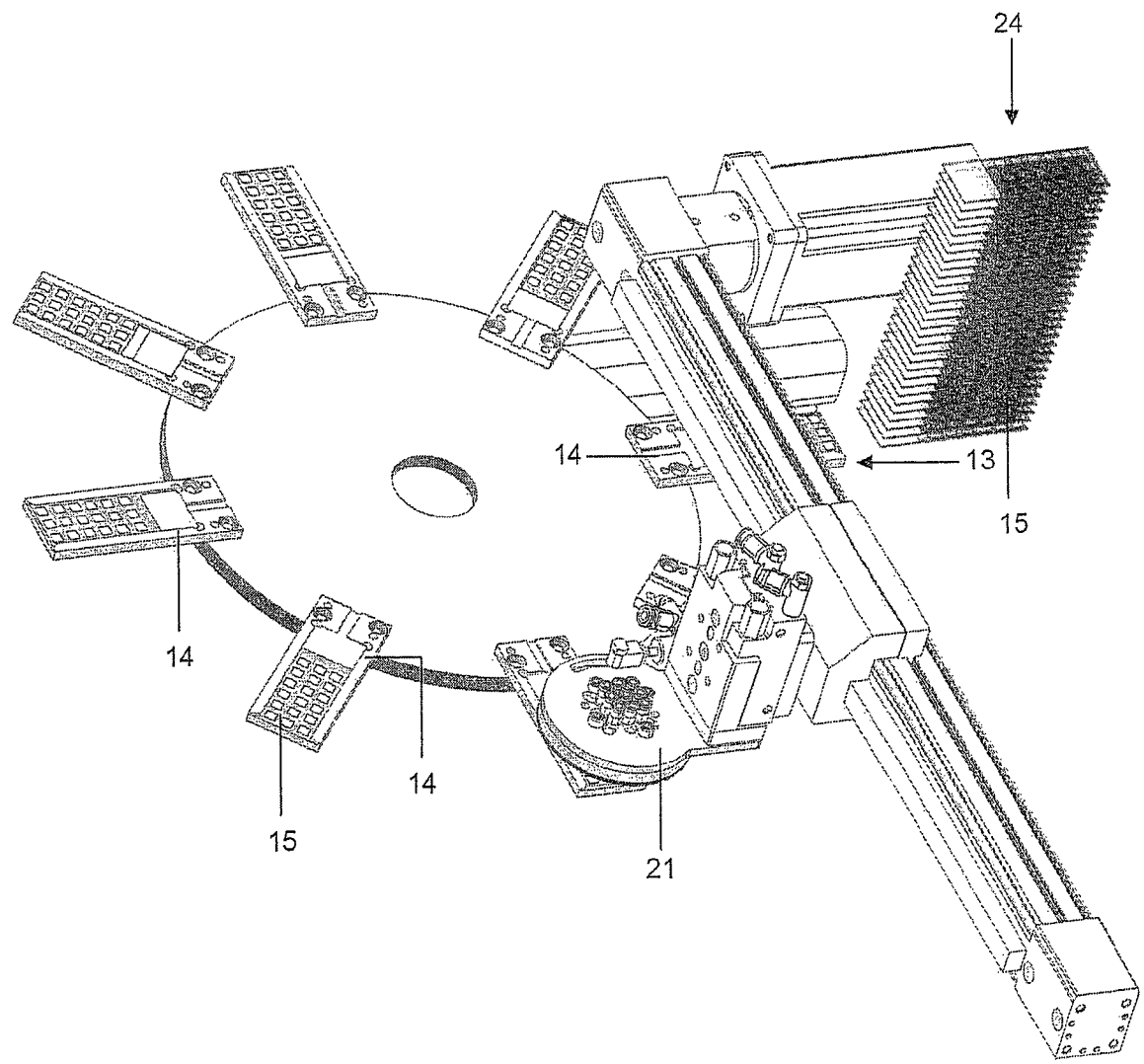
FIG. 10 a perspective view of the advance device with inserted slides and two processing stations arranged on the periphery.

FIG. 10 shows the advance device 8 more clearly, said device having arranged on its periphery equidistant receiving devices 14 for the specimen slides 15. The specimen slides are slid into these receiving devices 14 and fed to the individual processing stations in a cyclical manner. It is also obvious that a schematically indicated tray 24 with specimen slides 15 is arranged in the region of the input station 13, said individual specimen slides being successively supplied from said tray to the receiving device 14 at the input station 13.

Figure 11:
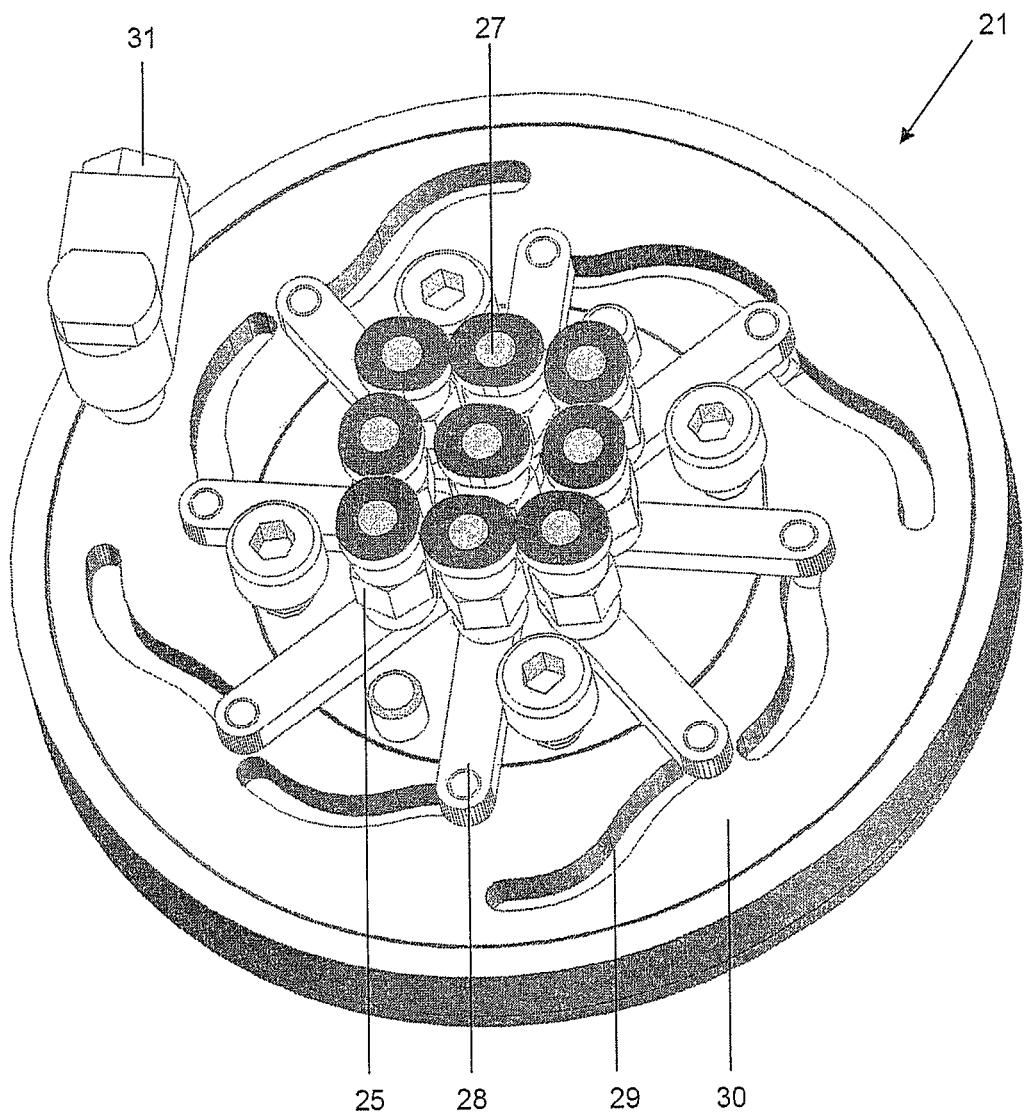
FIG. 11 a perspective view of the separating device, viewed from the top.

FIG. 11 shows a part of the separating device 21, where the upper plate has been left off for better visualization. It can be seen that nine cylinders 25 are provided, these being provided on their underside with pneumatically actuatable suction cups 26 and having, on their upper side, suction air connections 27. In so doing, the cylinders 25 are supported on the cam arms 28 which, in turn, are supported in the curved paths 29 of a plate cam 30 in a slidable manner. When the plate cam 30 is pivoted by means of the crank arm 31, the cam arms are forced to move in the curved paths, and the cylinders 25 move to prespecified positions on a larger radius. In this manner, the separated sample pieces adhering to the underside of the suction cups are separated in a specific array that corresponds exactly to the grid of the reaction fields of the specimen slide 15. As soon as the samples are in their intended exact position, they are deposited on the specimen slide 15 by means of the cylinder 25 and prevented by the adhesive from shifting.

Figure 12:
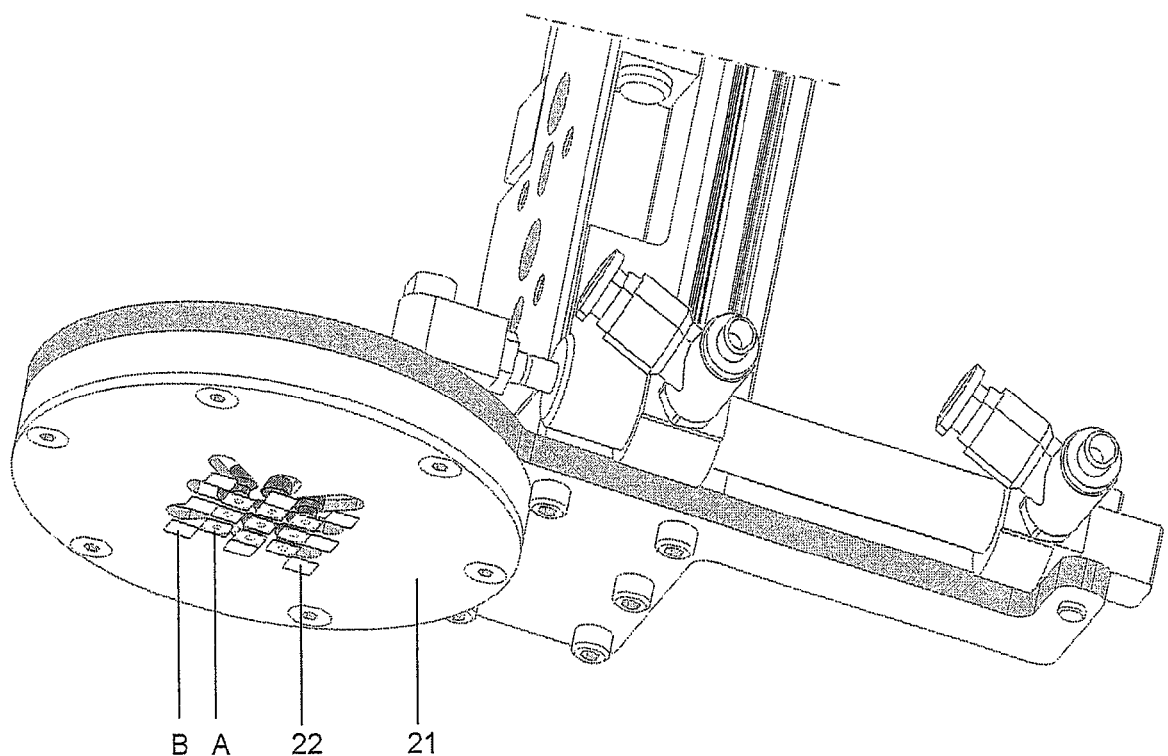
FIG. 12 a perspective view from the underside of the separating device.

FIG. 12 is a perspective view, from the bottom, of the separating device 21, in which the cell and tissue segments 22 are shown in the pushed together position X, in which they leave the punch, as well as in the separated position Y, in which they are deposited on the specimen slide 15.

Figure 13:
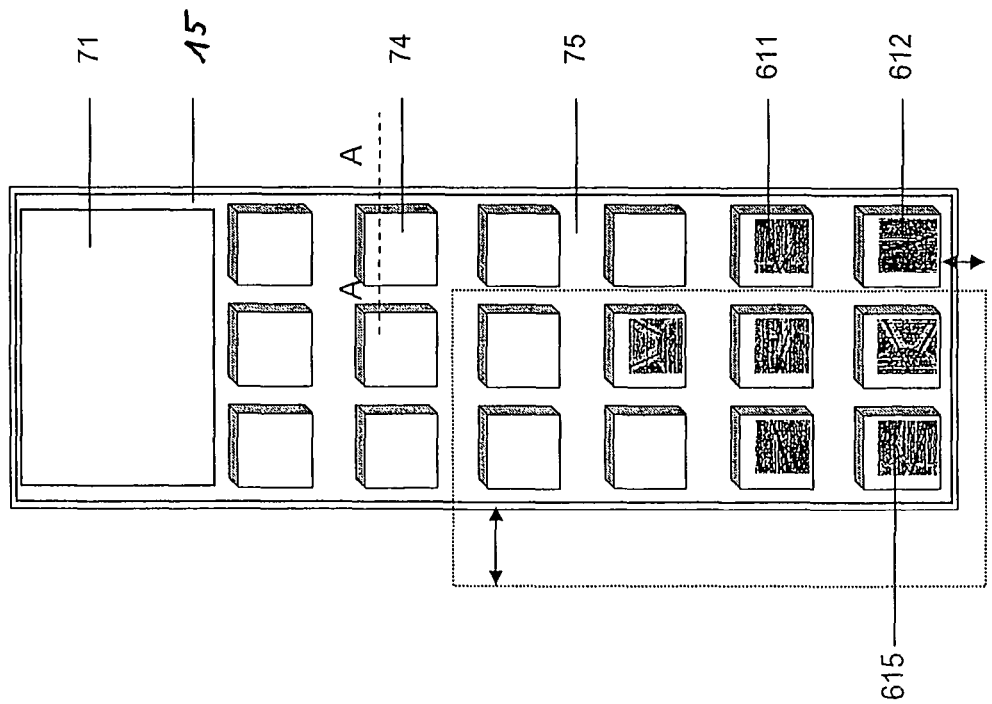
FIG. 13 an exemplary embodiment of a specimen slide in accordance with the invention.

FIG. 13 shows a specimen slide 15 as an exemplary embodiment of a specimen slide in accordance with the invention. A text field 71 is provided on the upper end, said field containing, for example, an identification code in the form of a barcode. The specimen slide 15 is coated, for example, with a sprayed-on frame, a Teflon film or a film of another hydrophobic material which contains recessed reaction zones 74. As an example, cell and tissue segments in the form of tissue/substrate units 611, 612 and 615 are shown in individual reaction zones. The dimensions of the specimen slide 15 are approximately 75×25 mm, and the dimensions of the cell and tissue segments are approximately 4×4 mm. Each specimen slide is loaded with 2 by 9 segments.

For example, the dimensions of a reaction zone are 4.5×4.5 mm, and the lateral edges along the bottom and the top are 1.8 mm each. The thickness of the film may be, for example, 0.13 mm, however, alternatively also 0.25 to 0.28 mm. Furthermore, a dashed line A-A is shown, it representing an intersection line of the illustration of FIG. 14.

Figure 14:
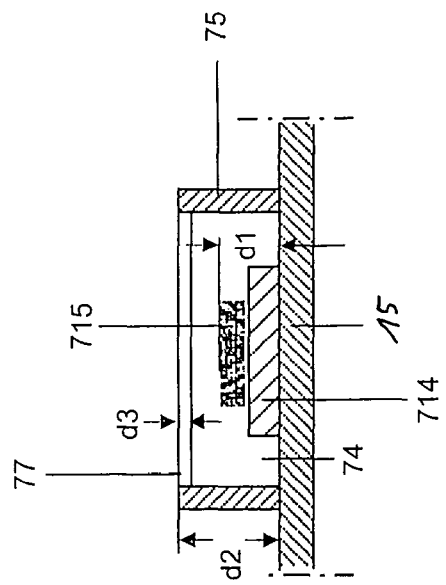
FIG. 14 illustrated by means of a section along line A-A, the dimensions of a reaction zone with the tissue/substrate unit inserted; and, FIG. 15 a schematic showing the loading of the processing reagents in the reaction zones on the slide.

FIG. 14 shows an example of a reaction zone 74. In the reaction zone 74, a cell and tissue segment is shown in the form of a tissue particle 715 arranged on a substrate 714, said tissue particle coming to be placed on a specimen slide 15. Considering this representation it should be noted in particular that the thickness d1, i.e., the sum of the thickness of the tissue section and the substrate is smaller than the thickness d2, i.e., the thickness of the carrier film 75, or a sprayed on border, whereby the thickness ratio is such that the reaction zone accommodates enough fluid in order to be able to process the tissue particle 715, but that, at the same time, no fluid is wasted. In this manner, it is ensured that, with the use of a defined fluid amount consistent with the thusly prespecified reaction volume as many tissue/substrate units can be processed or as many specimen slides as possible can be assayed.

Using such a specimen slide 18, assays can be combined on one and the same tissue and be simultaneously performed in a particular advantageous manner. Specifically, such a specimen slide can be sealed with a cover film, subsequently be archived in a patient-specific manner and be kept available for later observation.

Figure 15:
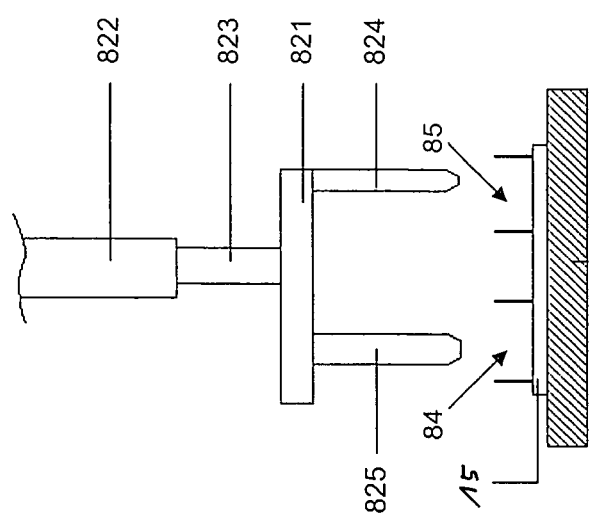

FIG. 15 is a schematic illustration of the subsequent treatment of the tissue/substrate units on the specimen slide 15 with reaction fluids. The apparatus comprises a hydraulic cylinder or a pneumatic cylinder that enables linear pushing movements and comprises an actuator 822 and, connected thereto, an actuator 823. Pipettes 825 and 824 are mounted to a bridge 821, said pipettes being at such a distance from each other that they can simultaneously dispense processing fluids into the reaction zones 84 and 85 of the specimen slide 15. In this manner, it is possible to simultaneously dispense several reaction fluids at the same time into different reaction zones of the specimen slide 15 in order to subject the slides that have been provided with the samples, after their completion, to the subsequent staining treatment by adding reaction fluids.

Advantageously, this apparatus that is an exemplary embodiment in accordance with the invention allows the simultaneous processing of several tissue/substrate units in the reaction zones of a specimen slide so that the most varied assays can be performed with the same tissue of one patient, for example, in a time-efficient manner. Of course, also other cell tissue types are conceivable such as, for example, biological tissue of animals, plants or seeds, but also adhering blood components, proteins or industrial materials that need to be subjected to such investigations.

Advantageously, the apparatus in accordance with the invention thus provides a combined processing and examination of the samples permitting several assays in an up-to-date manner. In particular, it is possible, for example to space the distances between the individual reaction zones in such a manner that they correspond to the pipette distances of a standard measure, for example, an ELISA (Enzyme-Linked Immunosorbent Assay) plate, whereby 6-, 8- or 12-channel pipettes may be used. The more channels are available, the more assays/processes can take place at the same time. This results in considerable time and cost savings.

Advantageously, this allows the use of standardized assay apparatus that only need to be adjusted to the specific case of application. Of course, it would be conceivable that the sample blocks as identified by number 31 in FIG. 3, be produced of the tissue of only one patient. To this extent, it would further be conceivable that, in accordance with the prior-art method, a specimen slide could be made available which contains only sample material of only one single patient. However, prior art does not offer any possibilities to provide this sample carrier with individual reaction zones or to subsequently divide the thin paraffin plate 32 with the tissue samples and accommodate them in separate reaction zones because this plate would be much too sensitive for this, and a defined reaction condition cannot be established in this manner.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by definition contained in the appended claims and equivalents thereof.

The invention claimed is:

1. Apparatus for the automated, reproducible production of cell or tissue samples to be examined and arranged on specimen slides, whereby the apparatus comprises a plurality of modular stations, each performing a process step as part of a total sequence of process steps, wherein the apparatus comprises at least one device for the correct positional arrangement of the samples on a specimen slide and for advancing the specimen slide to the modular stations for further processing, wherein the apparatus also comprises a separation device for separating the samples, wherein the separation device comprises a plate cam provided with cam arms and curved paths used for moving a plurality of gripping devices by way of said curved paths out of a substantially central position into a defined position at a distance relative to each of the other gripping devices.

2. Apparatus in accordance with claim 1, wherein the apparatus comprises an advance device located in the center of the apparatus and has modular stations distributed along a periphery of the advance device.

3. Apparatus in accordance with claim 2, wherein the advance device is a rotatably supported round table.

4. Apparatus in accordance with claim 2, wherein the advance device is a cyclically movable round table.

5. Apparatus in accordance with claim 2, wherein the advance device is a continuously program-controlled rotatable round table.

6. Apparatus in accordance with claim 2, wherein the advance device is supported by a pedestal-like housing which accommodates a drive and/or a control for the advance device.

7. Apparatus in accordance with claim 2, wherein the modular stations are arranged distributed in an array at constant angles relative to each other along the periphery of the advance device, so that they can be cyclically enabled.

8. Apparatus in accordance with claim 2, wherein the periphery of the advance device comprises receiving devices in which the specimen slides may be inserted in order to secure them in position during advance.

9. Apparatus in accordance with claim 1, wherein the apparatus comprises an input station through which a specimen slide can be supplied to the advance station.

10. Apparatus in accordance with claim 9, wherein the input station is allocated a slide tray from which the specimen slides can be successively supplied in a program-controlled manner.

11. Apparatus in accordance with claim 10, wherein the tray has a storage capacity of at least 150 specimen slides.

12. Apparatus in accordance with claim 1, wherein the apparatus has a station for fixation of the samples on the specimen slide.

13. Apparatus in accordance with claim 12, wherein the station for fixation of the samples comprises a dispenser for an adhesive for the application of discretely positioned metered amounts of adhesive having a defined size onto a specimen slide.

14. Apparatus in accordance with claim 13, wherein the adhesive is a type of UV adhesive.

15. Apparatus in accordance with claim 1, wherein the apparatus comprises a device for supplying a sample film provided with cell or tissue sections, said film consisting of a first transparent substrate, to a specimen slide, and comprises a punch for segmenting the samples.

16. Apparatus in accordance with claim 15, wherein the device for supplying the sample film, the punch and the separation device are combined in one work station.

17. Apparatus in accordance with claim 16, wherein the gripping devices are cylinders with pneumatically actuated suction cups.

18. Apparatus in accordance with claim 15, wherein the separation device is supported so as to be movable between the punch and the specimen slide.

19. Apparatus in accordance with claim 17, wherein the punch punches the samples out of the sample film against the picking devices.

20. Apparatus in accordance with claim 1, wherein the apparatus comprises a station for curing an adhesive.

21. Apparatus in accordance with claim 20, wherein the curing station is a UV-light irradiating device.

22. Apparatus in accordance with claim 1, wherein the apparatus comprises an inscribing and/or labeling station, in which the specimen slide is inscribed with a barcode or labeled.

23. Apparatus in accordance with claim 1, wherein the apparatus comprises a camera station for the visual detection of the individual samples and for the selection of suitable samples, as well as for the separation of unsuitable sample material.

24. Apparatus in accordance with claim 1, wherein the apparatus comprises a delivery station, in which the finished specimen slides are delivered to a subsequent device for continued processing.

25. Apparatus in accordance with claim 1, wherein the apparatus comprises a control panel that can be used to adjust controls for the adjustment of the process modes on the procession stations.

26. Apparatus in accordance with claim 1, wherein the apparatus comprises a frame of aluminum profiles, said frame being provided with a removable cover required to prevent operator intervention.

27. Apparatus in accordance with claim 1, wherein the apparatus is a table-top apparatus.

28. Apparatus in accordance with claim 1, further comprising the specimen slide, wherein the specimen slide has several reaction zones at a uniform first distance, and has tissue/substrate units in the reaction zones, whereby a substrate is flexible and transparent and, together with the cell and tissue samples, has a first thickness, and hydrophobic borders of the reaction zones have a first height.

29. Apparatus in accordance with claim 28, further including a cover applied over the reaction zones of the specimen slide in order to preserve the specimen slide or the tissue/substrate units in the reaction zones for later observation, whereby the cover has a second thickness.

30. Apparatus in accordance with claim 29, wherein considering the specimen slide the second thickness, the first height and the thickness of the specimen slide are so dimensioned in such a manner that they fit between a specimen slide of a microscope and a lens barrel of the microscope.

31. Apparatus in accordance with claim 29, wherein considering the specimen slide the first thickness and the first height are optimized with respect to a minimal fluid volume inside the border.

32. Apparatus in accordance with claim 28, whereby the first distance is so dimensioned as to correspond to the pipette distance of at least two jointly guided pipettes.

33. Apparatus in accordance with claim 28, wherein the specimen slide has a text field in which an identification code in the form of a barcode can be applied.

34. Apparatus in accordance with claim 28, wherein the reaction zones are formed by coating the specimen slide with a sprayed-on frame or with a film of a different hydrophobic material in which the reaction zones are recessed.

35. A method of using the apparatus of claim 28 comprising: using the apparatus for gene expression assays of human cell tissue.

36. Apparatus in accordance with claim 28, for the automated, reproducible production of cell or tissue samples to be examined and arranged on the specimen slides, wherein individual specimen slides are adapted to be continuously supplied via an input station to an advance device and fixed in position there, and that the advance device is adapted to successively supply each specimen slide to a fixing station for the application of a fixing agent, a loading station for the automatically registered loading of the specimen slide with segmented samples, a curing station for the fixing agent, an inscribing station, a scanner and reader station, and/or a camera station and a delivery station, where said specimen slides are delivered to a subsequent device for further processing.

37. Apparatus in accordance with claim 36, wherein the loading station is adapted to receive the samples in the form of a carrier film loaded with cell and tissue sections having a thickness of 1.5 μm, punched out of the film and separated, and deposited in a prespecified grid on the specimen slide that has been provided with a fixing agent.

38. Apparatus in accordance with claim 37, wherein the fixing agent is adapted to be cured in a subsequent treatment station by heat treatment.

39. Apparatus in accordance with claim 36, wherein the specimen slide delivered to the subsequent device is adapted to be subjected to a subsequent heat and staining treatment.

* * * * *